(12) United States Patent
Prywes

(10) Patent No.: US 9,675,335 B2
(45) Date of Patent: Jun. 13, 2017

(54) SURGICAL SLEEVES FOR SPECULUMS OR RETRACTORS AND A METHOD OF USING THE SAME

(71) Applicant: Arnold S Prywes, Bethpage, NY (US)

(72) Inventor: Arnold S Prywes, Bethpage, NY (US)

(\*) Notice: Subject to any disclaimer, the term of this patent is extended or adjusted under 35 U.S.C. 154(b) by 232 days.

(21) Appl. No.: 14/272,931

(22) Filed: May 8, 2014

(65) Prior Publication Data

US 2015/0320411 A1 Nov. 12, 2015

(51) Int. Cl.
*A61B 17/02* (2006.01)
*A61B 19/08* (2006.01)
*A61B 46/00* (2016.01)
*A61B 46/10* (2016.01)

(52) U.S. Cl.
CPC ........ *A61B 17/0231* (2013.01); *A61B 19/081* (2013.01); *A61B 46/00* (2016.02); *A61B 46/10* (2016.02)

(58) Field of Classification Search
CPC ......... A61B 46/00; A61B 46/10; A61B 46/13; A61B 46/17; A61B 46/20; A61B 46/23; A61B 46/27; A61B 46/30; A61B 17/0231
See application file for complete search history.

(56) References Cited

U.S. PATENT DOCUMENTS

| | | | | |
|---|---|---|---|---|
| 4,037,589 A * | 7/1977 | McReynolds | ...... | A61B 17/0231 600/209 |
| 4,412,532 A * | 11/1983 | Anthony | ............ | A61B 17/0231 600/206 |
| 5,213,114 A * | 5/1993 | Bailey, Jr. | .......... | A61B 17/0231 128/849 |
| 5,441,040 A * | 8/1995 | Williams, Jr. | ..... | A61B 17/0231 600/236 |
| 5,807,244 A * | 9/1998 | Barot | ................. | A61B 17/0231 600/236 |
| 6,345,621 B1 * | 2/2002 | Chandler | ........... | A61B 17/0231 128/849 |
| 6,382,211 B1 * | 5/2002 | Crook | ............... | A61M 16/0472 128/200.26 |
| 6,647,985 B1 | 11/2003 | Prywes | | |
| 2005/0115569 A1 * | 6/2005 | Davis | ................. | A61B 17/0231 128/849 |

(Continued)

FOREIGN PATENT DOCUMENTS

WO     WO 2004054487 A2 *  7/2004    ......... A61B 17/0231

*Primary Examiner* — Ellen C Hammond
(74) *Attorney, Agent, or Firm* — Ladas & Parry LLP

(57) ABSTRACT

A speculum drape for use in ophthalmic procedures. The speculum drape has at least a first sleeve made of surgical drape material that envelops at least a first retaining portion of a speculum or retractor. The sleeve is an elongate hollow structure with first and second open ends through which at least the first retaining portion is insertable. The sleeve is adapted and arranged such that, with the first retaining portion of the speculum or retractor inserted into the sleeve and with the speculum or retractor in an operating position with the respective retaining portions of the speculum or retractor engaged with opposite edges of an eyelid of a patient, the sleeve (i) envelops the inserted first retaining, (ii) is maintained in a disposition between the inserted retaining portion and the eyelid of the patient solely by compressive force and (iii) covers an eyelash of the patient.

14 Claims, 5 Drawing Sheets

(56) References Cited

U.S. PATENT DOCUMENTS

2007/0270657 A1* 11/2007 Stephenson .............. A61B 1/32
600/236
2011/0275903 A1 11/2011 Shelton
2015/0359529 A1* 12/2015 Ganiban ............ A61B 17/0231
600/203

* cited by examiner

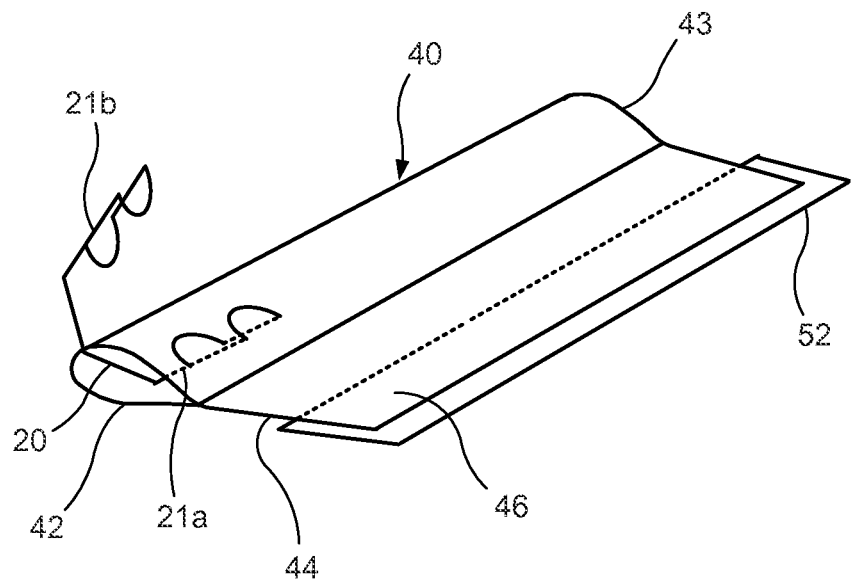
F I G. 3A
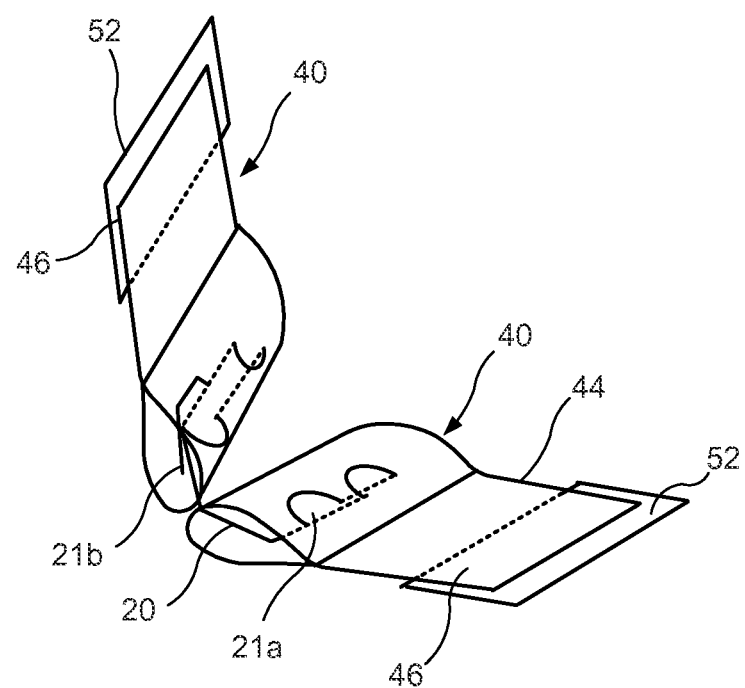
F I G. 3B

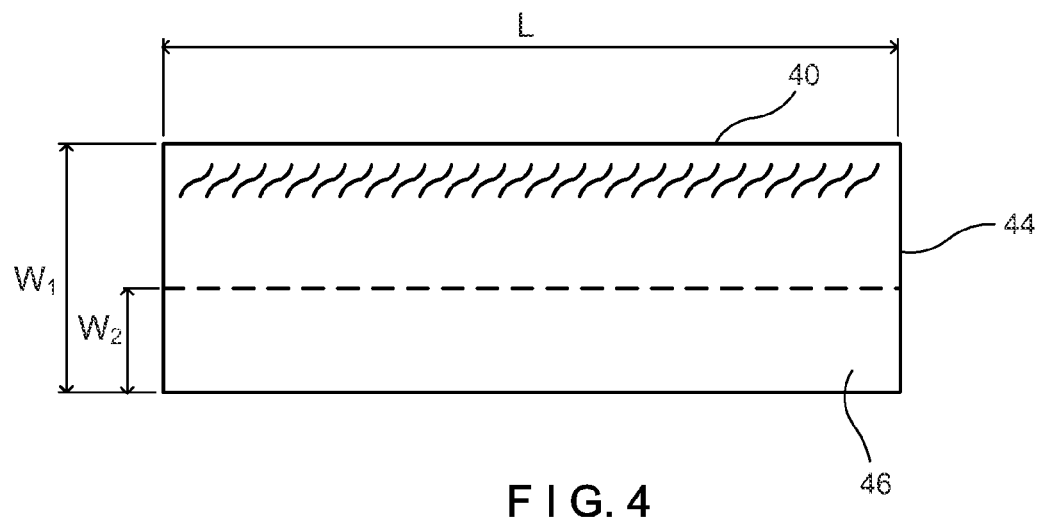
F I G. 4
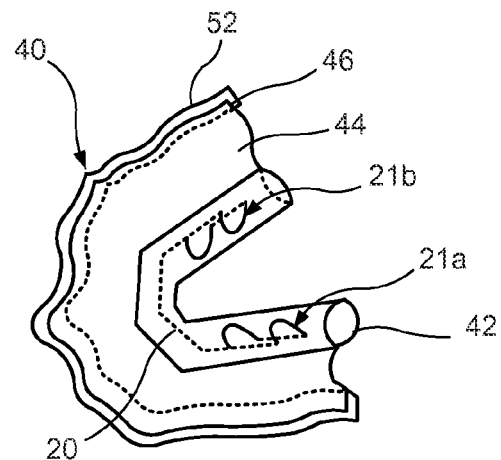
F I G. 5

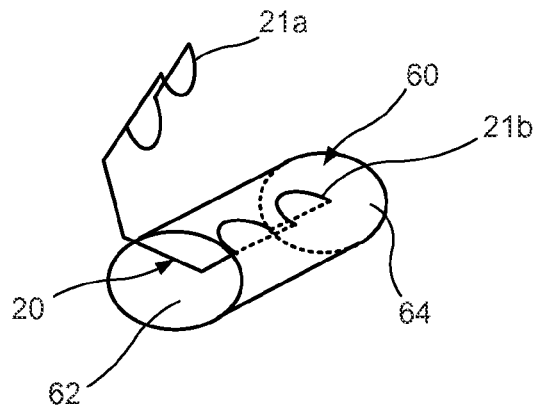
F I G. 7A
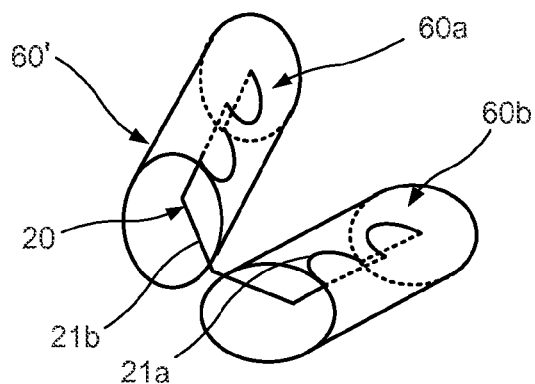
F I G. 7B
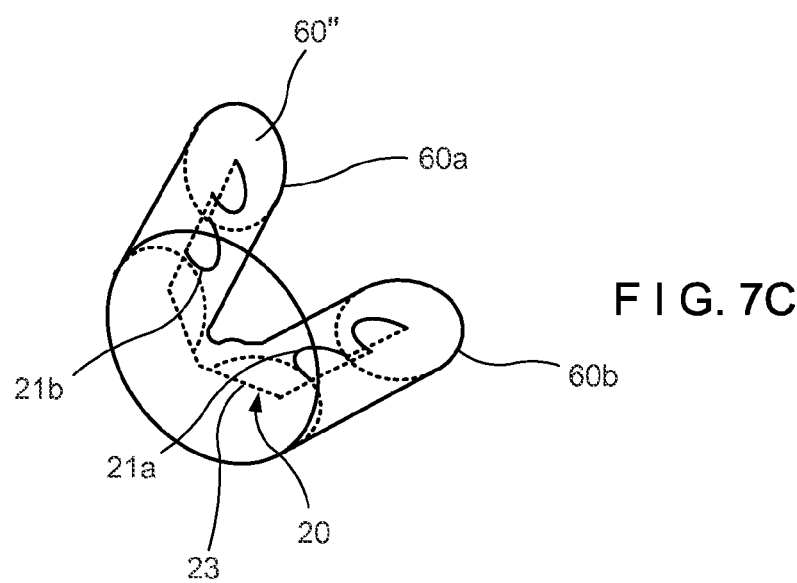
F I G. 7C

SURGICAL SLEEVES FOR SPECULUMS OR RETRACTORS AND A METHOD OF USING THE SAME

FIELD OF THE INVENTION

The invention relates to a barrier surgical sleeve drape for use with a speculum or retractor in an ophthalmic procedure.

BACKGROUND OF THE INVENTION

Ophthalmic procedures are typically performed after the tissue is cleansed with antiseptic solutions and draped with sterile drapes of cloth or plastic material. Typically the plastic material is adherent to the tissues to act as a barrier to contamination of the surgical site. The drape usually has an opening for incising the exposed tissue and for manipulation of the tissues within this opening. After entry into the tissues, the use of fluid, suction or wiping during the procedure often results in disruption of the adhesion of the drape to the external tissues. When a speculum or retractor is used to hold tissues away from a surgical field, no barrier between the speculum and the surgical site exists when the drape loses its adhesion. Often the drape may bunch together and obscure the view during the procedure. The lack of adhesion may result in bacterial entry into the surgical wound, possibly causing infection. In ocular surgery, the lid retractors or speculums often will not hold the eyelashes away from the surgical site thereby impeding the performance of the procedures.

Plastic drapes from different manufacturers have varying degrees of adhesion to underlying tissue surfaces and their loss of adhesion often causes the sterile drape surrounding the surgical site to loosen from the underlying tissues and to impede the movement of the surgical instruments by obstructing the path to the surgical site. The result of these difficulties with surgical draping produces increased difficulty in performing the ophthalmic procedure, increased time wasted in adjusting the drape resulting in prolonged operative and anesthesia times, placing patients in long procedures.

The speculum drapes of the prior art include the drapes described in the inventor's own U.S. Pat. No. 6,647,985, which describes a speculum drape comprising a sheet of surgical drape material having an opening of a size corresponding to a site in the eye of a patient and attachment means for attaching the drape material to an elastic surgical speculum or retractor so that the opening in the surgical drape material is positioned at said site. The attachment means comprises a plurality of projecting tabs for engaging the speculum or retractor to be secured therewith. The projecting tabs are wrapped around a portion of the speculum or retractor to secure the drape thereto.

US patent application 2011/0275903 to Shelton describes a surgical eye drape with first and second drape sections having a wing extending from each edge with a flap for forming a pouch disposed between the wings. In use, the drape sections are disposed under the eyelids of a patient's eye and the blades of a speculum are then inserted into a flap with inner and outer portions and a margin there between. The flap portions are then folded and adhered to each other to form a pouch or pocket which surrounds the speculum on three sides.

It may be appreciated that the surgical eye drape described in Shelton has a number of deficiencies. For example, the pouch or pocket must be introduced between the lid and globe to work. This means that, if the space between the inner surfaces of the pouch collapse or adhere to each other (such as by capillary action if the pouch gets wet or there is a static electric effect), it becomes difficult to have the speculum blade enter into the pouch. Moreover, even when the speculum blade is inserted into the pouch, the pouch does not surround the speculum and could be dislodged thereby exposing the eyelid during an ophthalmic procedure. Furthermore, manipulation is required to place the drape into the fornix of the eyelid-globe area before the speculum is inserted into the pouch and additional manipulation is required to fold the drape between the ocular and eyelid surfaces. This makes it difficult to drape the eyelid and speculum. The difficulty with insertion and retention of the drape is exacerbated by the need to place the drape within the fornix prior to insertion of the speculum.

Thus, notwithstanding the description of speculum drapes in the aforementioned patent and patent publication (the contents of which are hereby expressly incorporated herein by reference), there is a need for an improved speculum drape which is easier to use and/or provides better retention of the drape and/or protection against contamination during ophthalmic procedures.

SUMMARY OF THE INVENTION

In accordance with a first embodiment of the invention, there is provided an article adapted for use with a speculum or retractor in an ophthalmic procedure, wherein the speculum or retractor is configured such that it is deployable in an operating position with respective first and second retaining portions (e.g., blades) of the speculum or retractor engaging with and exerting force against respective opposite edges of an eyelid of a patient to hold apart the opposite edges. The article is made of surgical drape material and comprises a sleeve portion and a drape portion, the drape portion comprising first means for detachably affixing the article to a speculum drape or to the skin of a patient; the sleeve portion comprising an elongate, hollow member with open first and second ends through which the first or second retaining portion is insertable and second means for enveloping at least the first retaining portion of the speculum or retractor such that, with the sleeve portion enveloping the at least first retaining portion and with the speculum or retractor in the operating position, the speculum or retractor holds the opposite edges of the eyelid apart with the sleeve portion disposed between the at least first retaining portion and the eyelid and with the sleeve portion held in engagement with the eyelid by compressive force.

In a preferred aspect of this embodiment, the sleeve portion is held in engagement with the eyelid solely by compressive force and without any tab or other portion of the sleeve portion wrapped around the retainer portion of the retractor. The second means can further comprise a second elongate hollow sleeve for enveloping the second component of the speculum or retractor and having first and second open ends through which the second component of the speculum or retractor is insertable.

In another preferred aspect of this embodiment the sleeve portion is configured such that, with the speculum or retractor in the operating position with the sleeve portion enveloping the at least first component and disposed between the at least first component and the eyelid, the sleeve portion covers an eyelash of the patient.

In yet another preferred aspect of this embodiment, the sleeve portion and the drape portion of the article comprise a unitary piece of material that is integrally formed. The first means for detachably affixing the article to a speculum drape can comprise an adhesive covered by a peel back strip that is removable at a time when the article is desired to be adhered to the surgical drape by means of the adhesive.

In another aspect of the invention, there is provided a kit comprising the article according to this first embodiment and a speculum or retractor. In accordance with this aspect, the speculum or retractor comprises at least one blade with a loop having legs with an opening for straddling an edge of the eyelid.

In accordance with a second embodiment of the invention, there is provided a kit comprising:

(a) a speculum or retractor made of resilient material and comprising first and second means for engaging with and exerting force to hold apart respective opposite edges of an eyelid of a patient when the speculum or retractor in an operating position; and (b) at least a first sleeve made of surgical drape material, said sleeve being shaped to envelop at least the first means and having first and second open ends through which at least the first means is insertable into the sleeve, the sleeve being configured such that, with the first means inserted into the sleeve and with the speculum or retractor in the operating position, the sleeve envelops the inserted means and is maintained in a disposition between the inserted means and the eyelid solely by compressive force.

In accordance with one aspect of this embodiment, the sleeve is configured such that the speculum or retractor, including both the first and second means, is insertable into the sleeve. The kit may comprise at least a second sleeve made of surgical drape material and being of enveloping shape and having first and second open ends through which at least the second means is insertable. The speculum or retractor may comprise a blade comprising at least one loop having legs with an opening for straddling an edge of the eyelid.

In yet another embodiment of the invention, there is provided a method for draping an eye for an ophthalmic procedure comprising the steps of:

(a) providing a speculum or retractor made of resilient material and comprising first and second retaining portions for engaging with and exerting force to hold apart respective opposite edges of an eyelid of a patient when the speculum or retractor is disposed in an operating position with the first and second blades at the respective outer edges of the eyelid and the speculum or retractor is released;

(b) enveloping the first and second components with a sleeve or a plurality of sleeves made of surgical drape material;

(c) disposing the speculum or retractor in the operating position with the first and second blades at the respective outer edges of the eyelid; and (d) releasing the speculum or retractor so that the first and second blades engage with and exert force to hold apart the respective opposite edges of the eyelid with the sleeve or plurality of sleeves disposed between the first and second blades and the respective opposite edges of the eyelid and with the sleeve or plurality of sleeves held in engagement with the eyelid by compressive force, In one aspect of this embodiment, the enveloping in step (b) is performed without any adhesive, tab or other means for securing the sleeve to the speculum or retractor components, and the sleeve or plurality of sleeves is held in engagement with the eyelid solely by the compressive force.

BRIEF DESCRIPTION OF THE DRAWING FIGURES

Figure 6A:
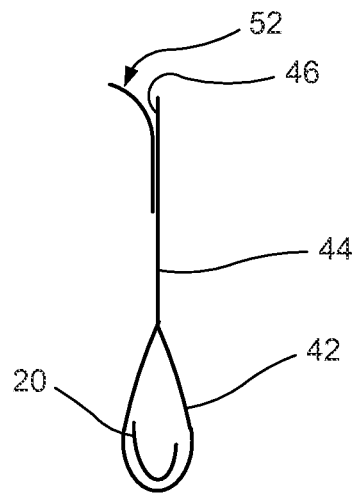

FIGS. 3A and B are perspective views of a speculum drape according to a first embodiment of the invention, wherein the sleeve of the speculum drape is shown enveloping one blade of a speculum (FIG. 3A), and wherein the respective sleeves of two of the speculum drapes are shown enveloping respective blades of a speculum (FIG. 3B);

FIG. 4 is a plan view of a one piece speculum drape according to the first embodiment;

FIG. 5 is a perspective view of a speculum drape according to another aspect of the first embodiment, wherein a single sleeve of the speculum drape envelops both blades of a speculum;

FIGS. 6A and B are cross sectional views of speculum drapes of the first embodiment showing the sleeve of the speculum drape in a teardrop shape (FIG. 6A) and in an indented, teardrop shape (FIG. 6B); and FIGS. 7A-C are perspective views of a speculum drape according to a second embodiment of the invention, wherein a single blade of a speculum is enveloped inside a hollow sleeve (FIG. 7A), wherein both blades of a speculum are enveloped inside two hollow sleeves (FIG. 7B), and wherein both blades of a speculum are enveloped inside a single hollow sleeve (FIG. 7C).

DETAILED DESCRIPTION

Figure 1:
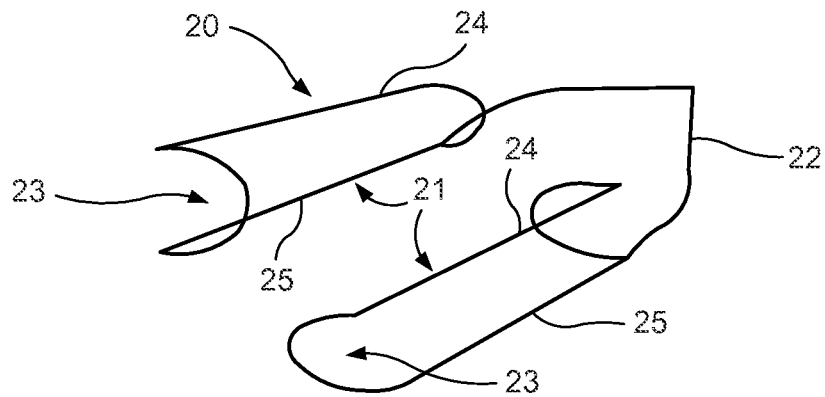
FIG. 1 is a perspective view of a conventional surgical speculum or retractor with which the speculum drape according to the invention is adapted to cooperate.

FIG. 1 shows a conventional speculum or retractor 20 adapted to engage opposite edges of an eyelid of a patient to hold the edges away from one another so as to facilitate an ophthalmic procedure. The retractor is made of a resilient material, such as a wire. The resilient wire of the speculum or retractor 20 is formed with two opposite retainer portions 21, which are joined by a connection portion 22 to provide lateral resiliency by which the retainer portions 21 can be urged towards and away from one another. The retainer portions 21 are bent to a U-shape to define openings 23 into which the edges of the eyelid can be inserted. The retainer portions 21 each have upper legs 24 and lower legs 25. The edges of the eyelid are received in openings 23 while the retainer portions 21 are pressed towards one another so that, when the retainer portions are released, the edges of the eyelid are kept away from one another.

Figure 2:
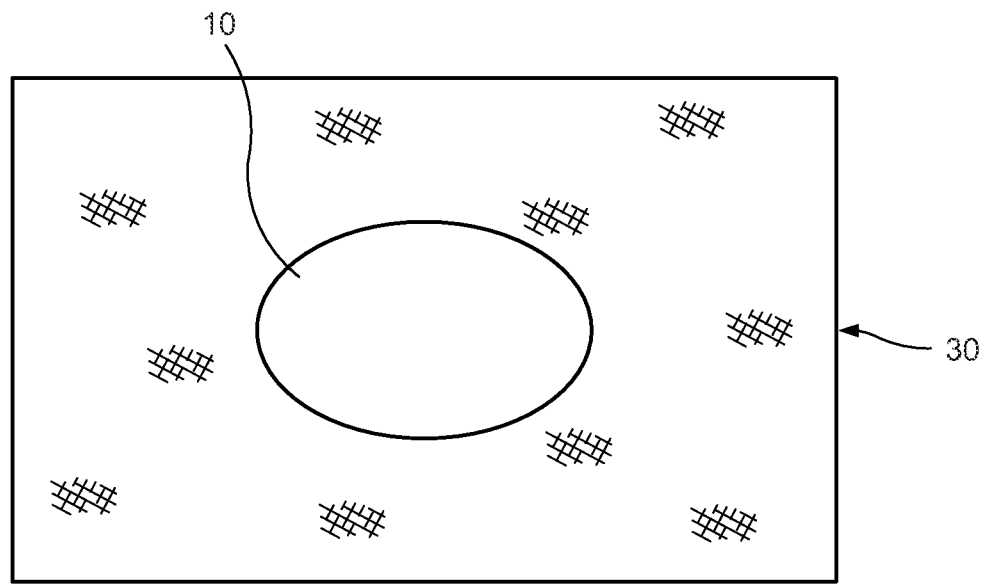
FIG. 2 shows a conventional surgical drape.

In normal use, when a surgical incision is to be made, the patient is covered with a surgical drape 30 having an opening 10 of a size corresponding to the dimensions of the size of an eye, as shown in FIG. 2. The speculum 20 is applied after the incision has been made. In the course of an operation in which the surgical drape 30 is used, the drape 30 can become bunched up or displaced away from the retractor and can interfere with the operation or no longer provide the antiseptic protection for surrounding tissue. The speculum drape of the invention avoids this and other problems, including at least some of the problems discussed previously.

FIGS. 3A and 4 show a speculum drape 40 according to a first embodiment of the invention. The speculum drape comprises an elongate, hollow sleeve portion 42 and a flat, drape portion 44. The flat, drape portion 44 has an end portion 46 with a top or back surface to which, in a preferred embodiment, adhesive is applied to facilitate adherence of the speculum drape 40 to a surgical drape 30 or to the skin of a patient. In the embodiment depicted in FIGS. 3A and 4, the end portion 46 extends an entire length L of the speculum drape, but this is not critical as one or more parts of the end portion 46 can be cut out without impairing its function. In the preferred embodiment depicted in FIGS. 3A and 4, there is a peel back strip 52 covering the adhesive to protect the adhesive until such time as the speculum drape is ready for use. At that time, the strip 52 can be peeled back to expose the adhesive and the speculum drape can then be adhered to the surgical drape 30 or to the skin of a patient.

Figure 6B:
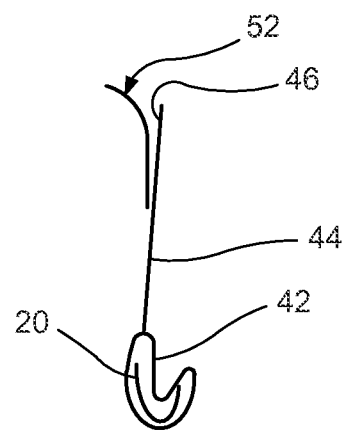

The shape of sleeve portion 40 is not critical so long as the sleeve portion is hollow, is of sufficient length to envelop at least one blade or retainer portion 21 of the speculum and has at least one end 42 that is open and unobstructed to permit insertion and/or removal of retainer portion 21 into and/or out of the sleeve portion. Thus, the sleeve portion 42 can be a hollow tube that, in cross section, has a tubular shape, as shown in FIG. 6A. FIG. 6B depicts the configuration that the hollow tube of FIG. 6A assumes when the speculum is pressed on the lid causing the drape to conform to the speculum's shape.

Although the sleeve portion 40 need only have one open end, for practicality and ease of use, it is preferably open at both of its ends 42 and 43. The sleeve portion 42 will preferably be made of a flexible material, such as polyethylene or polypropylene, so that a surface of the sleeve portion will conform to the shape of an inserted speculum blade or retainer portion when the sleeve with inserted retainer portion is compressed against the eyelid of a patient upon release of the retainer portion.

With reference to FIG. 4, in a preferred embodiment, the sleeve portion will have a length L of 1.5 to 2.5 inches and a width W1 of 0.75 to 1.75 inches. The end portion 46 will preferably have a width W2 of 0.5 to 1.0 inches.

FIG. 3B depicts an embodiment of the invention comprising two (2) speculum drapes constructed and arranged as discussed above with respect to the speculum drape 40 of FIG. 3A. In this embodiment, the sleeve portions 42a and 42b of the speculum drapes 40a and 40b envelop respective retainer portions 21a and 21b of speculum 20.

FIG. 5 depicts an embodiment of the invention wherein a single speculum drape 40 envelops the entire speculum 20, including both retainer portions 21a and 21b.

FIGS. 7A-C depict an alternative, preferred embodiment of the invention, wherein a speculum drape made of surgical drape material comprises at least one elongate hollow sleeve 60 that is shaped to envelop one or both retainer portions 21a and 21b of a speculum 20. The speculum 20 is made of resilient material and is configured such that retainer portions 21a and 21b may be pressed towards one another so as to be made to engage with opposing edges of an eyelid of a patient such that, when the retainer portions are released, the retainer portions exert a force against the edges of the eyelid to keep them away from one another.

A significant feature is that the flexible material (such as plastic) surrounding the speculum essentially serves as a sleeve drape for the eyelid. Once the material is placed onto the speculum (as a hollow tube) and disposed onto the lid margin, the drape would be impeded from slipping. The compression of the material onto the lashes prevents the lashes from escaping and keeps the plastic in place.

The speculum and sleeve drape could be an integral unit. Alternatively, it could be the hollow tube(s) with adhesive attaching the hollow tube(s) to an underlying drape. There could be separate tubes for each of the arms of the speculum to attach each of the individual sleeve drapes to an underlying drape. It is also possible for the hollow tube(s) to be affixed to the skin of a patient.

As shown in FIG. 7A, sleeve 60 is of tubular shape with first and second ends 62 and 64 through which retainer portion 21b of speculum 20 is insertable. The sleeve 60 is made of elastic material that is compressible such that, with the retainer portion 21b inserted into the sleeve 60 and with the retainer portions 21a and 21b pressed towards each other and holding the opposing edges of the eyelid apart, the sleeve 60 envelops the inserted retainer portion 21b and can be maintained in a disposition between the inserted retainer portion 21b and the eyelid solely by compressive force. The sleeve 60 has the dimensions and extent to cover and hold down the eyelashes of an eye of the patient to prevent the eyelashes from interfering with and causing contamination during an ophthalmic procedure. The sleeve 60 will preferably be made of a flexible material, such as polyethylene or polypropylene, so that a surface of the sleeve portion will conform to the shape of an inserted retainer portion of a speculum when the sleeve with inserted retainer portion is compressed against the eyelid of a patient upon release of the retainer portions.

FIG. 7B depicts another version of this embodiment wherein speculum drape 60' comprises two (2) separate sleeves 60a and 60b into which the respective retainer portions 21a and 21b of speculum 20 can be inserted through respective ends of the sleeves. With the retainer portions 21a and 21b so inserted, the sleeves 60a, 60b of the speculum drape envelop the respective portions 21a and 21b. In use during an ophthalmic procedure, each of the sleeves 60a, 60b can be held between the respective retainer portions 21a and 21b and opposite edges of a patient's eyelid to cover and hold down the patient's eyelashes during an ophthalmic procedure.

FIG. 7C depicts yet another version of the embodiment depicted in FIGS. 7A and 7B, wherein a speculum drape 60' is a unitary structure that comprises two (2) sleeves 60a and 60b that are incorporated into a single, integral structure that envelops in entirety speculum 20, including retainer portions 21a and 21b and connecting portion 23 that connects the retainer portions.

As with the other embodiments of the invention, the sleeve 60 will preferably be made of a flexible material, such as polyethylene or polypropylene, so that a surface of the sleeve will conform to the shape of an inserted speculum blade or retainer portion when the sleeve with inserted retainer portion is compressed against the eyelid of a patient upon release of the retainer portion. Also as with the other embodiments of the invention, the sleeve 60 does not need any adhesive, tab or other means for securing the sleeve to the speculum or retractor components, because the sleeve or plurality of sleeves can be held in engagement with the eyelid solely by compressive force. This provides a simple and effective way to provide a barrier between the speculum or retractor and the surgical site which avoids the difficulties discussed previously.

Although the invention is disclosed with reference to particular embodiments thereof, it will become apparent to those skilled in the art that numerous modifications and variations can be made which will fall within the scope and spirit of the invention as defined by the attached claims.

What is claimed is:

1. An article adapted for use with a speculum or retractor in an ophthalmic procedure, wherein the speculum or retractor is made of a resilient material and is configured such that it is deployable in an operating position wherein respective first and second retaining portions of the speculum or retractor engage with and exert force against respective opposite edges of an eyelid of a patient to hold apart the opposite edges; said article being made of sterile material and comprising a sleeve portion and a drape portion, wherein the sleeve portion and the drape portion of the article are integrally formed, the drape portion comprising first means for detachably mounting the article to a speculum drape or to skin of the patient; the sleeve portion comprising an elongate, hollow member with open first and second ends through which the first or second retaining portion is insertable, and configured for enveloping at least the first retaining portion of the speculum or retractor such that, with the sleeve portion enveloping the at least first retaining portion and with the speculum or retractor in the operating position, the speculum or retractor holds the opposite edges of the eyelid apart with the sleeve portion disposed between the at least first retaining portion and the eyelid and the sleeve portion engaged with the eyelid by compressive force, wherein the sleeve portion comprises at least a first sleeve of tubular, teardrop or indented tubular or teardrop shape with first and second open ends through which the first component of the speculum or retractor is insertable, and wherein the article further comprises a second elongate hollow sleeve portion for enveloping the second component of the speculum or retractor and having first and second open ends through which the second component of the speculum or retractor is insertable.

2. The article according to claim 1, wherein the sleeve portion is configured such that, with the speculum or retractor in the operating position with the sleeve portion enveloping the at least first retaining portion and disposed between the at least first retaining portion and the eyelid, the sleeve portion covers an eyelash of the patient.

3. The article according to claim 1, wherein the drape portion comprises an end portion with a top or back surface to which adhesive is applied.

4. A kit comprising the article according to claim 1 and a speculum or retractor.

5. The kit according to claim 4, wherein the speculum or retractor comprises at least one blade with a loop having legs with an opening for straddling an edge of the eyelid.

6. A kit comprising:
(a) a speculum or retractor made of resilient material and comprising first and second means for engaging with and exerting force to hold apart respective opposite edges of an eyelid of a patient when the speculum or retractor is disposed in an operating position with the first and second means at the respective outer edges of the eyelid and the speculum or retractor is released, wherein the first means comprises a thin resilient material formed into a loop having legs with an opening for straddling an edge of the eyelid; and
(b) at least a first sleeve made of sterile material, said sleeve being dimensioned to envelop at least the loop of the thin resilient material and having at least one open end through which at least the loop of the thin resilient material is insertable into the sleeve, the sleeve being configured such that, with the loop of the thin resilient material inserted into the sleeve and with the speculum or retractor in the operating position, the sleeve (i) envelops the loop of the thin resilient material, (ii) is maintained in a disposition between the loop of the thin resilient material and the eyelid solely by compressive force and (iii) covers an eyelash of the patient, wherein the sleeve is made of a flexible material such that the compressive force causes the sleeve to change shape and to conform to the configuration of the loop of the thin resilient material.

7. The kit according to claim 6, comprising at least a second sleeve made of sterile material and being of enveloping shape and having first and second open ends through which at least the sleeve portion is insertable.

8. The kit according to claim 6, wherein the loop of the thin resilient material is of U shape.

9. The kit according to claim 6, wherein, prior to being caused to conform to the configuration of the loop of the thin resilient material by the compressive force, the sleeve is of tubular shape.

10. The kit according to claim 6, wherein the sleeve has two open ends.

11. A kit comprising:
(a) a speculum or retractor made of resilient material and comprising first and second means for engaging with and exerting force to hold apart respective opposite edges of an eyelid of a patient when the speculum or retractor is disposed in an operating position with the first and second means at the respective outer edges of the eyelid and the speculum or retractor is released; and
(b) at least a first sleeve made of sterile material, said sleeve being shaped to envelop at least the first means and having first and second open ends through which at least the first means is insertable into the sleeve, the sleeve being configured such that, with the first means inserted into the sleeve and with the speculum or retractor in the operating position, the sleeve (i) envelops the first means, (ii) is maintained in a disposition between the first means and the eyelid solely by compressive force and (iii) covers an eyelash of the patient, wherein the sleeve is configured such that the speculum or retractor, including both the first and second means, is insertable into the sleeve.

12. A method for draping an eye for an ophthalmic procedure comprising the steps of:
(a) providing the kit of claim 6;
(b) enveloping the loop of the thin resilient material with the sleeve made of sterile material;
(c) disposing the speculum or retractor in the operating position with the opening straddling a first edge of the eyelid; and
(d) releasing the speculum or retractor so that the first and second means engage with and exert force to hold the first edge apart from an opposite second edge of the eyelid with the sleeve disposed between the loop of the thin resilient material and the first edge of the eyelid and with the sleeve or held in engagement with the eyelid by compressive force.

13. The method according to claim 12, wherein the enveloping in step (b) is performed without any adhesive.

14. The method according to claim 12, wherein the sleeve is held in engagement with the eyelid solely by the compressive force.

* * * * *